US010531668B2

(12) United States Patent
Steffens et al.

(10) Patent No.: US 10,531,668 B2
(45) Date of Patent: Jan. 14, 2020

(54) METHOD AND APPARATUS FOR INSPECTING THE ABDOMINAL CAVITY OF GUTTED FISH

(71) Applicants: NORDISCHER MASCHINENBAU RUD. BAADER GMBH + CO. KG, Lübeck (DK); IHFOOD A/S, Kopenhagen (DK)

(72) Inventors: Alexander Steffens, Lübeck (DE); Carsten Paulsohn, Lübeck (DE); Niels Tjørnly Rasmussen, Hvidovre (DK); Eigil Mølvig Jensen, Kopenhagen S (DK); Ulrik Nielsen, Kopenhagen K (DK)

(73) Assignees: NORDISCHER MASCHINENBAU RUD. BAADER GMBH + CO. KG, Lübeck (DE); IHFOOD A/S, Kopenhagen N (DK)

( * ) Notice: Subject to any disclaimer, the term of this patent is extended or adjusted under 35 U.S.C. 154(b) by 0 days.

(21) Appl. No.: 16/096,086

(22) PCT Filed: Apr. 26, 2016

(86) PCT No.: PCT/EP2016/059307
§ 371 (c)(1),
(2) Date: Oct. 24, 2018

(87) PCT Pub. No.: WO2017/186275
PCT Pub. Date: Nov. 2, 2017

(65) Prior Publication Data
US 2019/0116810 A1     Apr. 25, 2019

(51) Int. Cl.
*A22B 5/00* (2006.01)
*A22C 17/00* (2006.01)
(Continued)

(52) U.S. Cl.
CPC .............. *A22B 5/007* (2013.01); *A22C 17/008* (2013.01); *A22C 25/00* (2013.01); *A22C 25/04* (2013.01);
(Continued)

(58) Field of Classification Search
CPC .......... A22B 5/00; A22B 5/0064; A22B 5/007
(Continued)

(56) References Cited

U.S. PATENT DOCUMENTS 5,980,376 A    11/1999   Grosseholz
6,649,412 B1   11/2003   Borggaard
(Continued)

FOREIGN PATENT DOCUMENTS

EP     1 003 378     2/1999
EP     1 411 775     2/2003
WO     96/03887      2/1996

OTHER PUBLICATIONS

PCT Search Report and Written Opinion issued in PCT/EP2016/059307.
(Continued)

*Primary Examiner* — Richard T Price, Jr.
(74) *Attorney, Agent, or Firm* — Greenblum & Bernstein, P.L.C.

(57) ABSTRACT

The present invention relates to an apparatus for optical inspection of the opened abdominal cavity (10) of gutted fish (11), comprising a conveying device (12) configured for conveying the fish (11) along a processing line in the longitudinal direction, pivotable ventral flaps holding elements (17) configured for holding open the abdominal cavity (10) of the fish, at least one optical imaging system (21, 22, 23) arranged along the processing line, said optical imaging system being designed and configured to take at least one sequence of images of abdominal cavity regions of one of
(Continued)

the fish (11) in each case, said sequence comprising a plurality of single images, at least one illumination device (24, 25) configured for illuminating the abdominal cavity regions in each case with light of a predetermined spectral composition, in each case at the times the single images are taken, an evaluation unit (26) configured to evaluate the image sequence according to prescribed quality parameters, said evaluation unit being designed to activate an ejection device to remove the relevant fish (11) from the processing line by ejecting it, should the evaluation reveal any deviation from the prescribed quality parameters. The invention further relates to a corresponding method.

24 Claims, 7 Drawing Sheets

(51) Int. Cl.
    | | |
    |---|---|
    | *A22C 25/00* | (2006.01) |
    | *A22C 25/04* | (2006.01) |
    | *A22C 25/08* | (2006.01) |
    | *G01N 21/25* | (2006.01) |
    | *G01N 21/95* | (2006.01) |
    | *G01N 33/12* | (2006.01) |
    | *G05B 19/416* | (2006.01) |
    | *G06T 7/00* | (2017.01) |
    | *H04N 5/235* | (2006.01) |

(52) U.S. Cl.
    CPC ........... *A22C 25/08* (2013.01); *G01N 21/255* (2013.01); *G01N 21/95* (2013.01); *G01N 33/12* (2013.01); *G05B 19/416* (2013.01); *G06T 7/0004* (2013.01); *H04N 5/2354* (2013.01); *G05B 2219/45054* (2013.01); *G06T 2207/10016* (2013.01); *G06T 2207/10152* (2013.01); *G06T 2207/20221* (2013.01); *G06T 2207/30128* (2013.01)

(58) Field of Classification Search
    USPC ........ 452/125, 129, 149–154, 160–163, 166, 452/167, 177, 179, 180, 182–184
    See application file for complete search history.

(56) References Cited

U.S. PATENT DOCUMENTS

| | | | | |
|---|---|---|---|---|
| 7,841,264 | B2* | 11/2010 | Kim | B26D 3/10 83/13 |
| 7,988,542 | B1* | 8/2011 | Yamase | A22C 25/16 452/150 |
| 8,092,283 | B2* | 1/2012 | Hansen | A22C 25/08 452/121 |
| 8,118,647 | B2* | 2/2012 | Mikajiri | A22C 25/14 452/149 |
| 8,387,522 | B2* | 3/2013 | Rusko | A22C 17/0086 99/540 |
| 2004/0023612 | A1 | 2/2004 | Kriesel | |
| 2004/0203331 | A1 | 10/2004 | Grobeholz | |

OTHER PUBLICATIONS

Anonymous: Salmol Gutting Revolution—BAADER dated Mar. 2016 at link: https://www.foodprocessing-technology.com/contractors/processing/baader/pressreleases/pressbaader-144-baader-1570.

Kroma A/s: "Gutmaster 3000—The perfect gutting machine for medium sized fish", XP055335179, retrieved from the internet: URL:http://www.kroma.df/wp-content/uploads/2015/06/090615_gm_3000.pdf [retrieved on Jan. 13, 2017], May 18, 2009.

Kroma A/s: "Visiomaster—The good result is now visible", XP055334652, Retrieved from Internet: URL:http://www.odimakine.com.tr/fileadmin/user_upload/BrosurMakinelerWebSitesi/8-Su/12-VisionMaster.pdf [retrieved on Jan. 12, 2017], May 22, 2008.

* cited by examiner

METHOD AND APPARATUS FOR INSPECTING THE ABDOMINAL CAVITY OF GUTTED FISH

BACKGROUND OF THE INVENTION

The present invention relates to a method for optical inspection of gutted fish with opened abdominal cavity. The invention further relates to a method for gutting fish which are conveyed along a processing line in the longitudinal direction by means of a conveying device.

In addition, the invention relates to an apparatus for optical inspection of the opened abdominal cavity of gutted fish as well as an apparatus for gutting fish which are conveyed along a processing line in the longitudinal direction by means of a conveying device.

Such apparatuses and methods are used in industrial fish processing. The fish are usually automatically slaughtered by opening the abdominal cavity of the fish and automatically removing the guts thereof using appropriate tools. The gutting result is usually checked optically. For this, the abdominal cavity of the fish in inspected with a colour camera subsequent to the gutting step and the image taken of the abdominal cavity is examined for any possible remaining residues of blood and/or gut using known image processing algorithms.

These known apparatuses and methods have a number of disadvantages. Due to the use of a colour camera, which splits the incident light into each of the primary colours by means of a Bayer filter, the effective resolution is significantly reduced compared to a monochrome camera. On the other hand, correspondingly long exposure times are required. This is contrary to the requirement for the highest possible conveying speed of the fish because the maximum conveying speed is severely limited due to the exposure time to be observed. An increase in the conveying speed results in blurred images of the abdominal cavity and thus overall to lower reliability of the image evaluation. A further disadvantage is that evaluation of the colour images is computing- and time-intensive.

SUMMARY OF THE INVENTION

It is therefore the object of the present invention to propose an apparatus and a method which guarantee a reliable optical inspection of the abdominal cavity with simultaneously high conveying speeds of the fish. The object is additionally to propose an apparatus and a method for gutting fish which enable the most reliable gutting result possible at high conveying speed.

The object is achieved by the apparatus referred to hereinbefore, the apparatus comprising a conveying device configured for conveying the fish along a processing line in the longitudinal direction, pivotable ventral flaps holding elements configured for holding open the abdominal cavity of the fish, at least one optical imaging system arranged along the processing line, said optical imaging system being designed and configured to take at least one sequence of images of abdominal cavity regions of one of the fish in each case, said sequence comprising a plurality of single images, at least one illumination device configured for illuminating the abdominal cavity regions, in each case with light of a predetermined spectral composition, in each case at the times the single images are taken, an evaluation unit configured to evaluate the image sequence according to prescribed quality parameters, said evaluation unit being designed to activate an ejection device to remove the relevant fish from the processing line by ejecting it, should the evaluation reveal any deviation from the prescribed quality parameters. This offers the advantage that the abdominal cavity regions are illuminated by means of the illumination devices with a prescribed colour of light or a light wavelength range and the single images are each taken by one of the optical imaging systems. By illuminating with coloured light, the respective wavelength range of interest is absorbed by means of the optical imaging system. A colour filter, for example a Bayer filter or similar, is no longer necessary in the optical imaging system. On the one hand this benefits the overall resolution of each of the optical imaging systems, on the other hand the intensity of the incident light is not attenuated by any filters. This favours short exposure times so that the fish can be transported at correspondingly high conveying speeds. A further advantage is that, due to active illumination by means of the illumination device, the fish or its abdominal cavity can be lit up with high-intensity light. The illumination devices are preferably made up of LED arrays. The illumination devices are further preferably each operated only for the duration of the required exposure time so that the regions to be lit up are illuminated in a flash. The present invention is therefore particularly suited to the optical inspection of fast moving objects.

An advantageous development of the invention is characterised in that the at least one illumination device is configured to illuminate the abdominal cavity region, in each case with light of different spectral ranges, at the times the images are taken. In this way, it is possible to inspect the abdominal cavity of the fish according to any quality characteristics with optimum adjustment. The light spectral ranges used are matched in each case to the structures to be identified. Actual evaluation of the image sequence is carried out using customary image evaluation algorithms that are based either on statistical methods or on the use of neural networks.

According to a preferred embodiment, the at least one illumination device comprises a light source which is configured to emit light of a narrow band spectrum. In this way, the selectivity for identifying specific structures is further increased.

According to a further advantageous embodiment of the invention, the apparatus comprises further control means which are designed and configured to control the at least one optical imaging system in such a way that the time interval between taking two consecutive single images of one of the image sequences is chosen such that the two consecutive single images at least substantially illustrate the same abdominal cavity region. This has a particularly advantageous effect on the complexity of image evaluation. Due to the short time interval between the images which is now possible, the continuous onward movement of each fish does not result in local displacement of the single images. It is therefore possible to dispense with otherwise necessary correction or 'mapping' of the image position in order to align the single images. This has a positive effect on the computing time required for evaluating the image sequence.

A preferred embodiment of the invention is characterised in that a plurality of the optical imaging systems are each arranged and configured separately along the processing line to take each of the single images with one of said optical imaging systems. In this way, reliable inspection is always guaranteed even at high conveying speeds.

According to an advantageous embodiment of the invention, each of the optical imaging systems is assigned a separate illumination device which is configured to illuminate the abdominal cavity regions, in each case at the times the images are taken. As already mentioned, it is thus possible to examine the relevant regions and structures with a high level of detection accuracy.

A further advantageous development is characterised in that the at least one optical imaging system is designed as a black and white camera. The use of black and white cameras enables high-resolution images and thus correspondingly high accuracy of the abdominal cavity inspection. In addition, they are correspondingly light-sensitive with the result that it is possible to implement the short exposure times or high conveying speeds referred to.

According to a further preferred embodiment, the at least one optical imaging system is arranged in such a manner that at least one of the single images is taken with a viewing direction onto the abdominal cavity that is vertical or at least substantially vertical. In this manner, the entire region of the abdominal cavity can be lit up optimally and any possible remaining residues can be reliably detected.

A further embodiment of the invention provides for at least one further optical imaging system being arranged in such a manner that at least one other of the single images is taken with a viewing direction that is inclined in relation to the vertical viewing direction. On the one hand, this enables the detection of areas that are in shadow during vertical illumination so that overall the detection quality and therefore the reliability of the abdominal cavity inspection is increased.

Advantageously, the at least one further optical imaging system is inclined in such a manner that in the inclined viewing direction the images are taken towards the head of the fish. In other words, an oblique image is taken with the direction of view from the tail towards the head. Added to the advantage mentioned above regarding inspection of the regions in shadow, it also offers the additional benefit of being explicitly able to inspect the head-end region of the abdominal cavity.

According to a preferred embodiment of the invention, the evaluation unit is configured to overlay the single images of the image sequence to create one overall image. The overall image is used, for example, as a control image to check the inspection process on a random basis. Alternatively, the overall image is used as a starting point for the optical inspection.

The object is also achieved by the apparatus, referred to hereinbefore, for gutting fish which are conveyed along a processing line in the longitudinal direction by means of a conveying device, comprising opening tools configured for opening the abdominal cavity of the fish, gutting tools designed for cleaning out the abdominal cavity and an apparatus for subsequent optical inspection of the abdominal cavity of the gutted fish as described above. The combination of the method according to the invention for optical inspection of the abdominal cavity and the upstream gutting process ensures a high-quality production workflow during which it is ensured that, after the gutting process, the fish meet the imposed quality requirements in respect of a cleaned abdominal cavity.

In addition, the object is achieved by the method referred to hereinbefore, comprising conveying the fish along a processing line in the longitudinal direction by means of a conveying device, pivoting of ventral flaps holding elements configured for holding open the abdominal cavity of the fish, taking at least one sequence of images of abdominal cavity regions of one of the fish, each, by means of an optical imaging system arranged along the processing line, said image sequence comprising a plurality of single images, illuminating the abdominal cavity regions with light of in each case a predetermined spectral composition by means of at least one illumination device, in each case at the times the single images are taken, evaluating the image sequence according to prescribed quality parameters and removal of the relevant fish from the processing line by ejecting it using an ejection device, should the evaluation reveal any deviation from the prescribed quality parameters.

The advantages associated with the method according to the invention have already been explained in detail above in connection with the apparatus according to the invention. To avoid repetition, reference is made to the relevant passages. This applies equally to the preferred embodiments of the method according to the invention referred to below.

A preferred embodiment of the invention is characterised in that the illumination takes place in each case with light of different spectral ranges at the times the images are taken. Illumination preferably takes place with light of a narrow band spectrum.

According to an advantageous development of the invention, the time interval between taking two consecutive single images of one of the image sequences is chosen such that the two consecutive single images at least substantially illustrate the same abdominal cavity region.

According to an advantageous development, it is provided that each of the single images is taken with a separate optical imaging system.

Advantageously, each of the optical imaging systems is assigned a separate illumination device by means of which the illumination takes place in each case at the times the images are taken.

A preferred embodiment of the invention is characterised in that the single images are taken in black and white.

According to an advantageous embodiment of the invention, at least one of the single images is taken with one of the optical imaging systems with a viewing direction onto the abdominal cavity that is vertical or at least substantially vertical.

It is further preferably provided that at least one other of the single images is taken with one other of the optical imaging systems with a viewing direction that is inclined in relation to the vertical viewing direction. In particular, it is advantageous for the images to be taken in the inclined viewing direction towards the head of the fish.

A preferred embodiment of the invention provides for single images of the image sequence to be overlaid to create one overall image.

The object is further achieved by the method, referred to hereinbefore, for gutting fish which are conveyed along a processing line in the longitudinal direction by means of a conveying device, the method comprising opening the abdominal cavity of the fish, cleaning out the abdominal cavity using gutting tools and subsequent optical inspection of the abdominal cavity of the gutted fish using the method described above.

Further preferred and/or expedient features and embodiments of the invention emerge from the dependent claims and the description. Especially preferred embodiments are explained in greater detail with reference to the attached drawing. The drawing shows:

BRIEF DESCRIPTION OF THE INVENTION

DETAILED DESCRIPTION OF THE INVENTION

The apparatus according to the invention and the method according to the invention will be described in greater detail in the following based on the drawing. To avoid repetition, the method according to the invention will also be explained based on the apparatus according to the invention. The statements made regarding the apparatus therefore also apply analogously to the method according to the invention.

Figure 1:
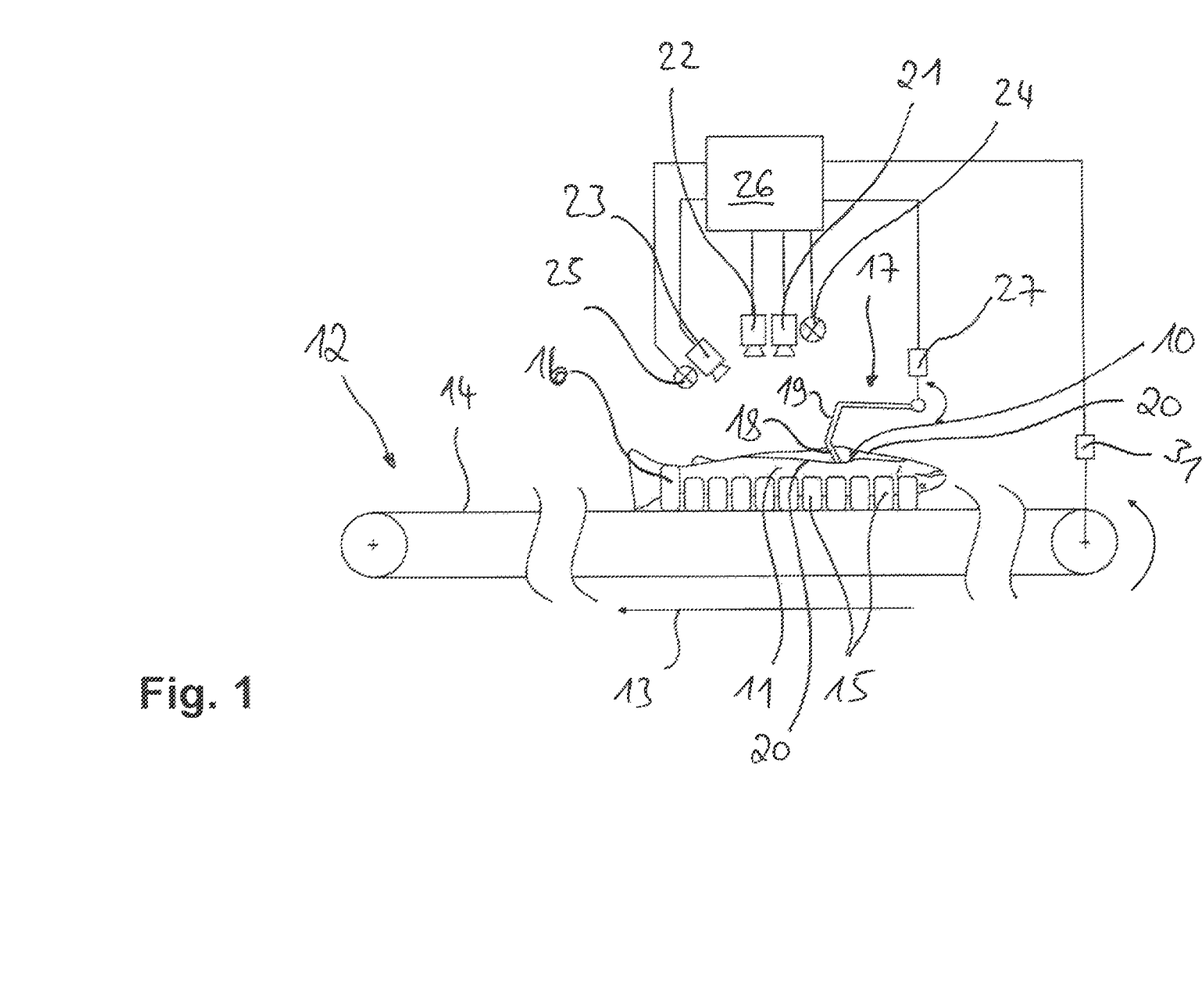
FIG. 1 a schematic diagram of the apparatus according to the invention in lateral view.

FIG. 1 shows a schematic diagram of the apparatus according to the invention in lateral view. The apparatus is designed and configured for optical inspection of the opened abdominal cavity 10 of gutted fish 11. The apparatus comprises a conveying device 12 configured for conveying the fish 11 along a processing line in the longitudinal direction 13. The conveying device 12 is designed, for example, as a rotating conveyor belt 14 with holding and centring means 15. The holding and centring means are configured to hold the fish 11 in the dorsal position and to align them so that they are conveyed in the longitudinal direction 13 with the opened abdominal cavity 10 pointing upwards. The holding and centring means 15 are preferably designed in a V shape. One each of the holding and centring means is designed as a tail clamp 16 which secures the relevant fish 11 against slipping in the longitudinal direction 13.

The apparatus according to the invention further comprises pivotable ventral flaps holding elements 17 for holding open the abdominal cavity 10 of the fish. The ventral flaps holding elements 17 preferably comprise a substantially V-shaped spreading bow 18 which is moved via a pivot lever 19 into the abdominal cavity 10 and back out of it again. The ventral flaps holding elements 17 are designed and configured to spread apart the ventral flaps of the opened abdominal cavity 10 of the fish 11.

At least one optical imaging system is arranged on the processing line, for example—as shown in FIG. 1—a first imaging system 21, a second imaging system 22 and a third imaging system 23. The present invention, however, is not limited to the number of imaging systems 21, 22, 23 shown but alternatively may also comprise fewer or more of the imaging systems 21, 22, 23. The imaging systems 21, 22, 23 are designed and configured to take at least one sequence of images of abdominal cavity regions of one of the fish 11 in each case, said image sequence comprising a plurality of single images.

Using a first illumination device 24 and a second illumination device 25, the abdominal cavity regions are illuminated, in each case with light of a predetermined spectral composition, in each case at the times the single images are taken. As shown in FIG. 1, the number of illumination devices is not limited to only two. Alternatively, it is also possible to employ only a single one of the illumination devices 24, 25 or to use more than two of the illumination devices 24, 25.

An evaluation unit 26 is designed and configured to evaluate the image sequence in respect of prescribed quality parameters and to activate an ejection device—not shown in the drawing—to remove the relevant fish 11 from the processing line by ejecting it, should the evaluation reveal any deviation from the prescribed quality parameters. The prescribed quality parameters relate, for example, to optical comparative values that provide information about the extent or degree to which the guts have already been removed. This also includes comparative values pertaining to blood residues or connective tissue residues. In addition, the quality parameters include variables for checking the correct position of the ventral incision.

The evaluation unit 26 is connected to the optical imaging systems 21, 22, 23, the first and second illumination devices 24, 25, an actuator 27 for moving the ventral flaps holding elements 17 and preferably to a drive 31 for driving the conveying device 12 such that the evaluation unit 26 can control or regulate the aforementioned components. The connections are preferably designed as electrical connections.

The first illumination device 24 and the second illumination device 25 are each configured to illuminate the abdominal cavity region, in each case with light of different spectral ranges at the times the images are taken. The spectral ranges each comprise a section of the visible or infra-red wavelength spectrum.

Preferably, the first illumination device 24 and the second illumination device 25 each comprise a light source which is configured to emit light of a narrow band spectrum. Narrow band means that the light covers a spectral range having a wavelength smaller than 100 nm. Especially preferably, the light is monochromatic in each case.

The evaluation unit 26 further comprises control means which are designed and configured to control the imaging systems 21, 22, 23 in such a way that the time interval between taking two consecutive single images of one of the image sequences is chosen such that the two consecutive single images at least substantially illustrate the same abdominal cavity region. In other words, the control means are configured, in coordination with the set conveying speed of the conveying device 12, to take the single images at such a time interval that each of the single images substantially shows the same region of the abdominal cavity 10.

Figure 2:
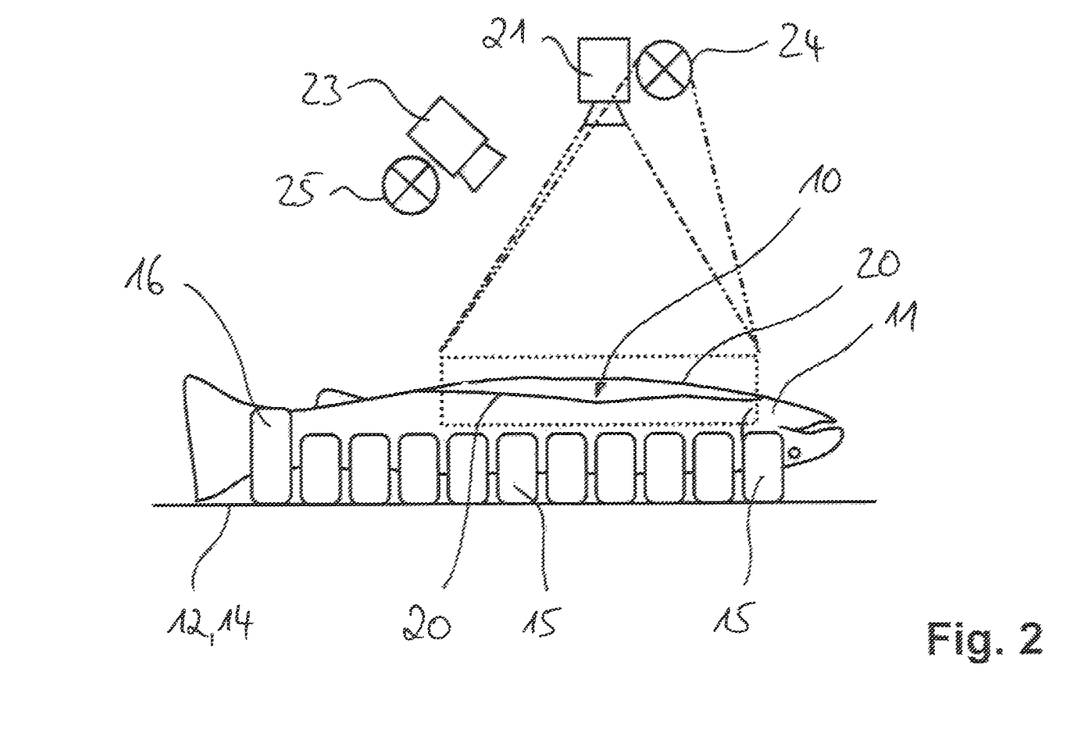
FIG. 2 a schematic diagram of a first process step according to the invention in detail, FIG. 3 a schematic diagram of a second process step according to the invention in detail, FIG. 4 a schematic detail view with a ventral flaps holding element in a waiting position of the apparatus according to the invention in lateral view.
Figure 3:
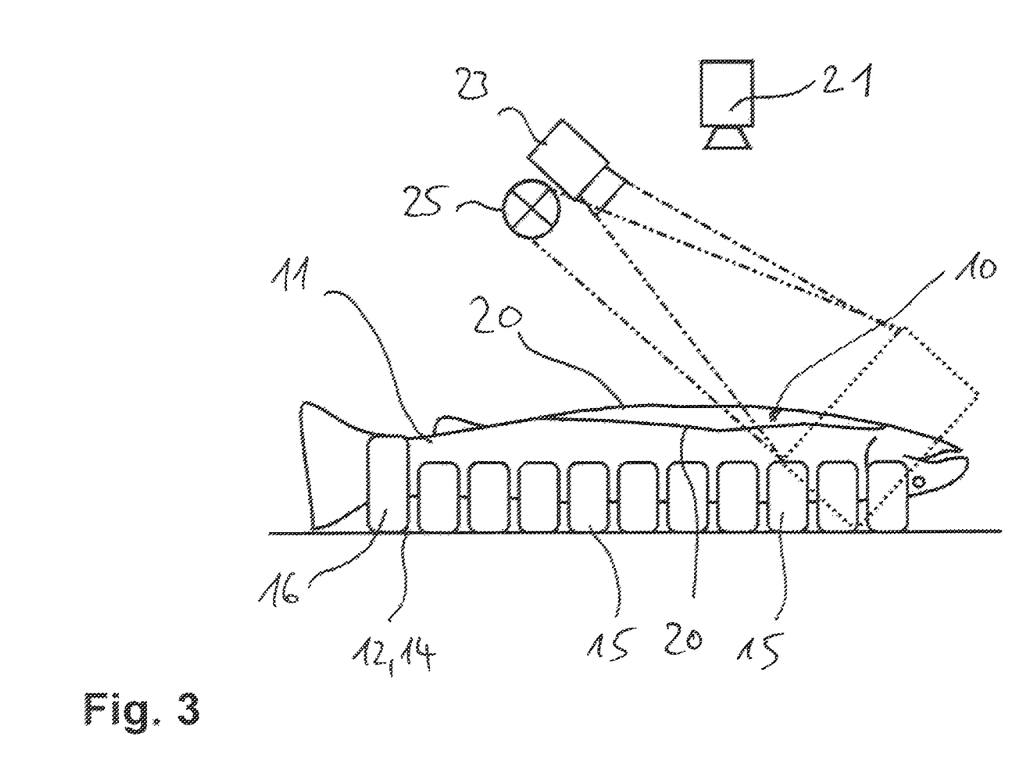

As can be seen from FIGS. 2 and 3, a plurality of optical imaging systems 21, 22, 23 are arranged along the processing line, in each case only the first imaging system 21 and the third imaging system 23 being illustrated in the detail views of FIGS. 2 and 3. The optical imaging systems 21, 22, 23 are preferably each arranged and configured separately to take each of the single images with one of the optical imaging systems 21, 22, 23. For the sake of clarity, the ventral flaps holding elements 17 which hold open the abdominal cavity 10 of each fish 11 for optical inspection are not shown in FIGS. 2 and 3.

Especially preferably, each of the optical imaging systems 21, 22, 23 is assigned a separate illumination means which is configured to illuminate the abdominal cavity regions in each case at the times the images are taken. As shown in FIGS. 2 and 3, the first illumination device 24 is assigned to the first imaging system 21 and the second illumination device 25 is assigned to the third imaging system 23.

According to an advantageous embodiment of the invention, the imaging systems 21, 22, 23 are each designed as a black and white or as a monochrome camera.

Alternatively, one or more of the imaging systems 21, 22, 23 in each case is designed as a colour camera.

At least one of the optical imaging systems 21, 22, 23 is preferably arranged in such a manner that at least one of the single images is taken with a viewing direction onto the abdominal cavity 10 that is vertical or at least substantially vertical. For this, for example, the first imaging system 21 and the first illumination device 24 are arranged—as shown in FIG. 2—above the conveying device 12.

As shown in FIG. 3, at least one further optical imaging system, for example the third imaging system 23, is arranged in such a manner that at least one other of the single images is taken with a viewing direction that is inclined in relation to the vertical viewing direction. In particular, the third imaging system 23 is inclined in such a manner that in the inclined viewing direction the images are taken towards the head of the fish.

The evaluation unit 26 is configured in particular to overlay the single images of the image sequence to create an overall image. The overall image may optionally be displayed for control purposes. The overall image is further used for quality control. The evaluation unit 26 is preferably configured to assemble the image sequence into a false colour image by weighting the single frames differently.

In particular, the imaging systems 21, 22, 23 and the illumination devices 24, 25 are preferably arranged encapsulated in a housing 28 with at least one viewing window 30.

Figure 4:
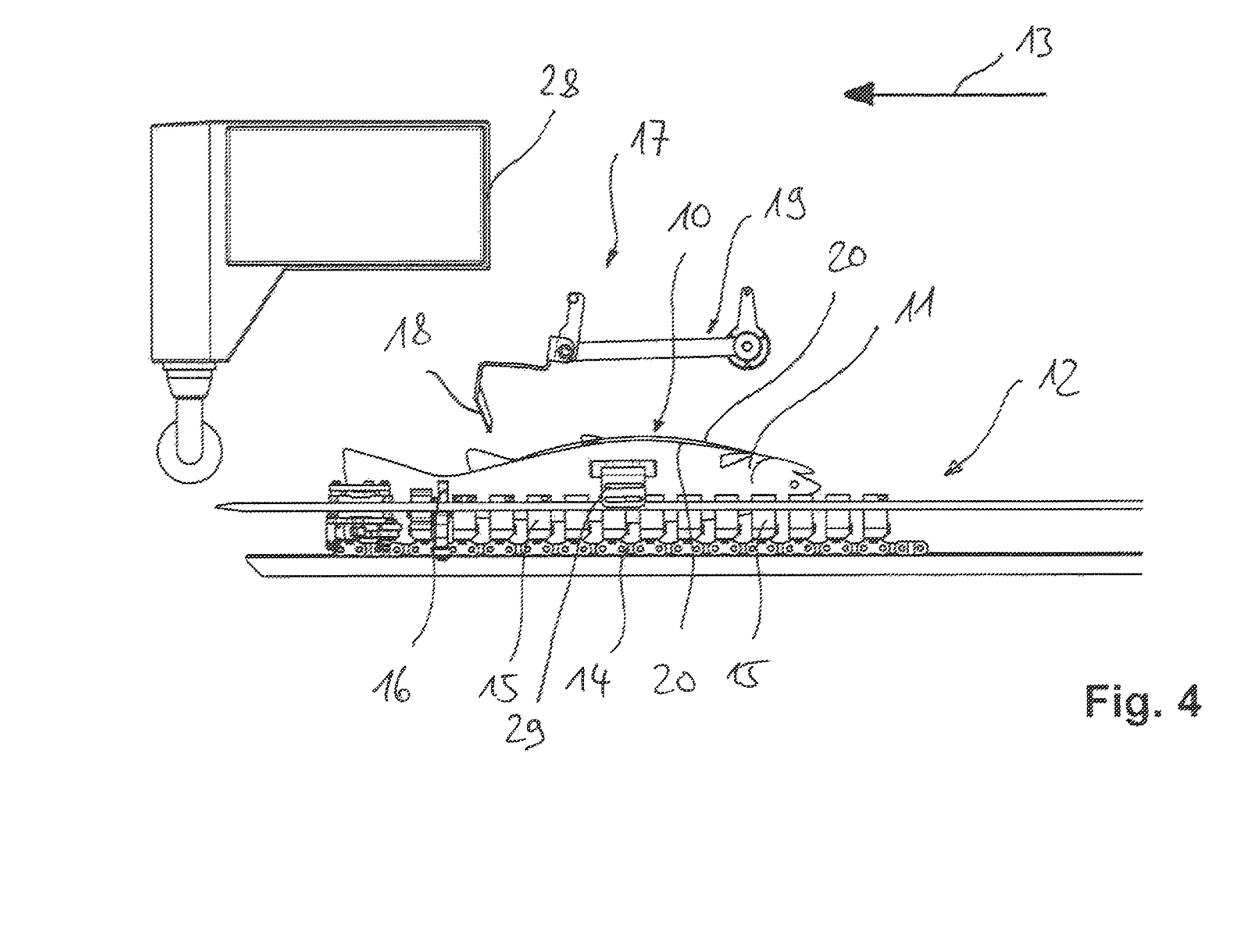
Figure 5:
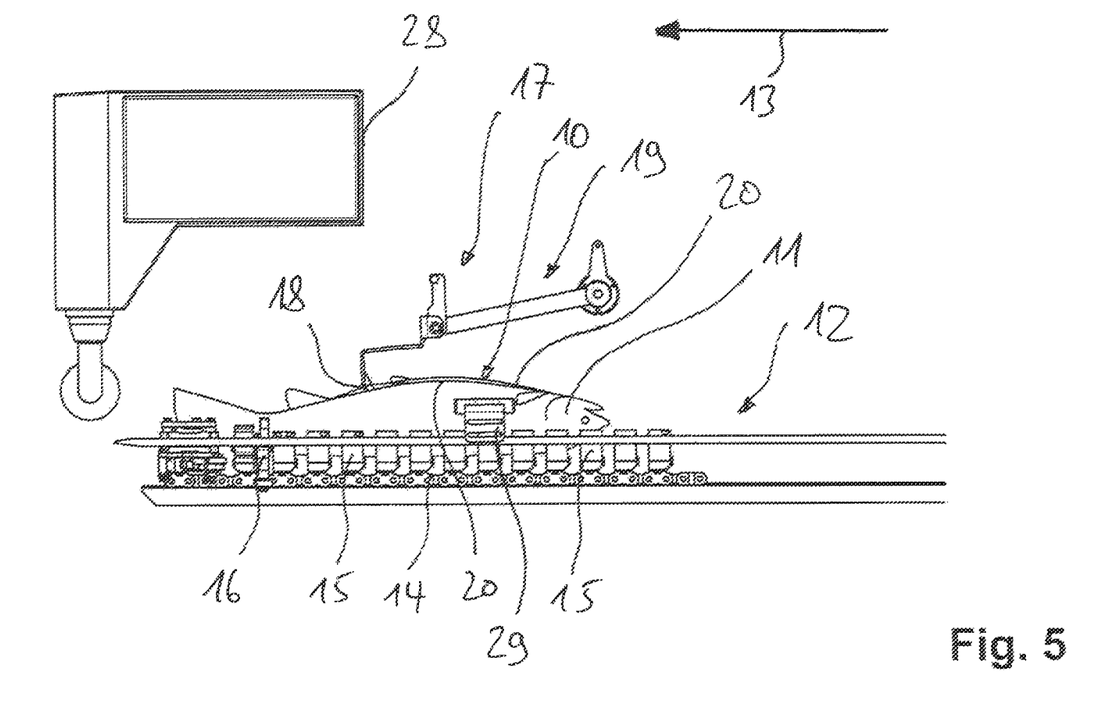
FIG. 5 a schematic detail view with a ventral flaps holding element in a working position of the apparatus according to the invention in lateral view, FIG. 6 a perspective view of the detail view illustrated in FIG. 4 and FIG. 7 a perspective view of the detail view Illustrated in FIG. 5.

FIG. 5 shows a schematic detail view with the ventral flaps holding elements 17 in a working position of the apparatus according to the invention in lateral view. The ventral flaps holding elements 17 are guided into the abdominal cavity and hold the ventral flaps 20 open laterally so that the abdominal cavity can be inspected. FIG. 4 shows how the ventral flaps holding elements 17 are in a waiting position outside the abdominal cavity.

Figure 6:
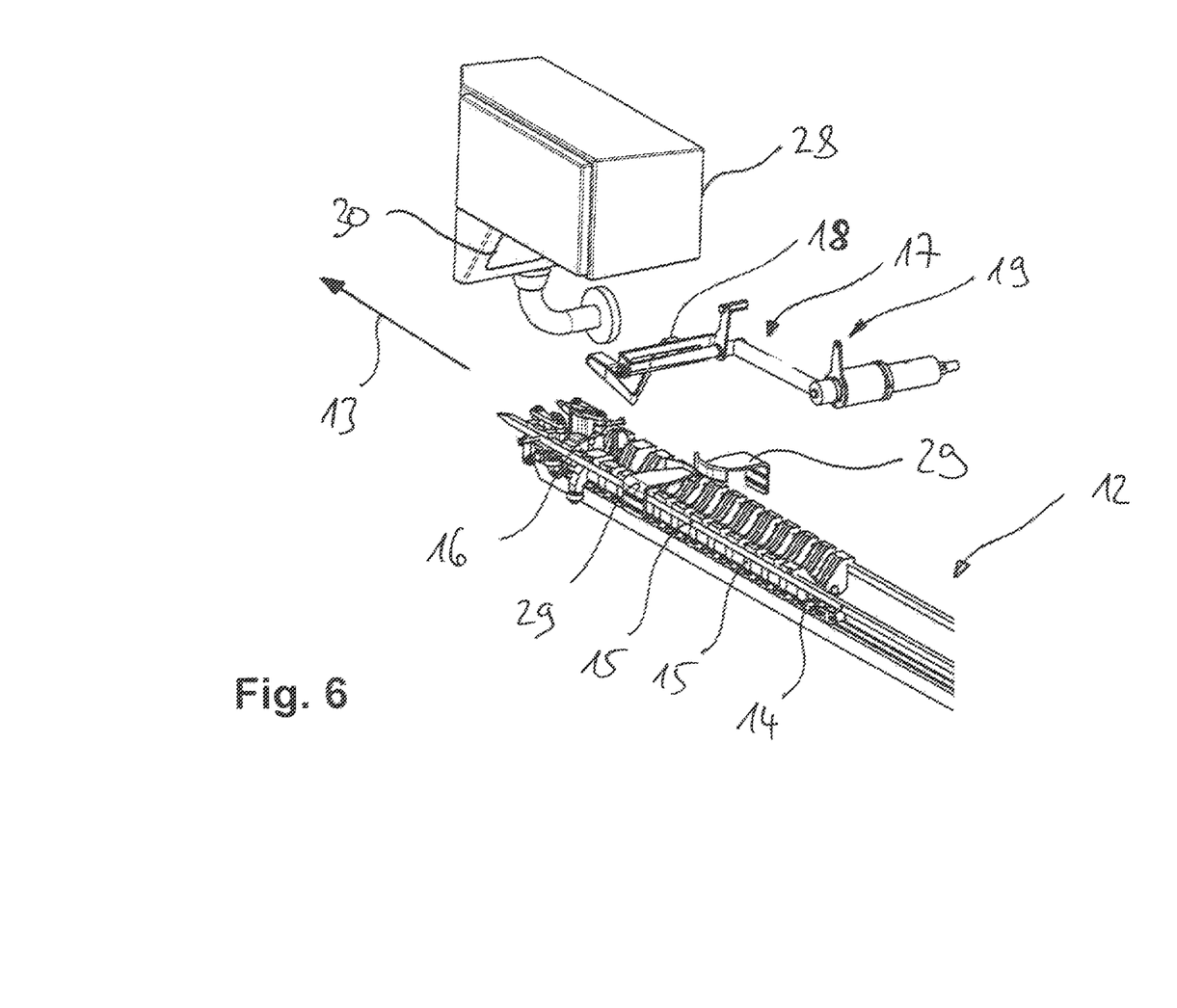
Figure 7:
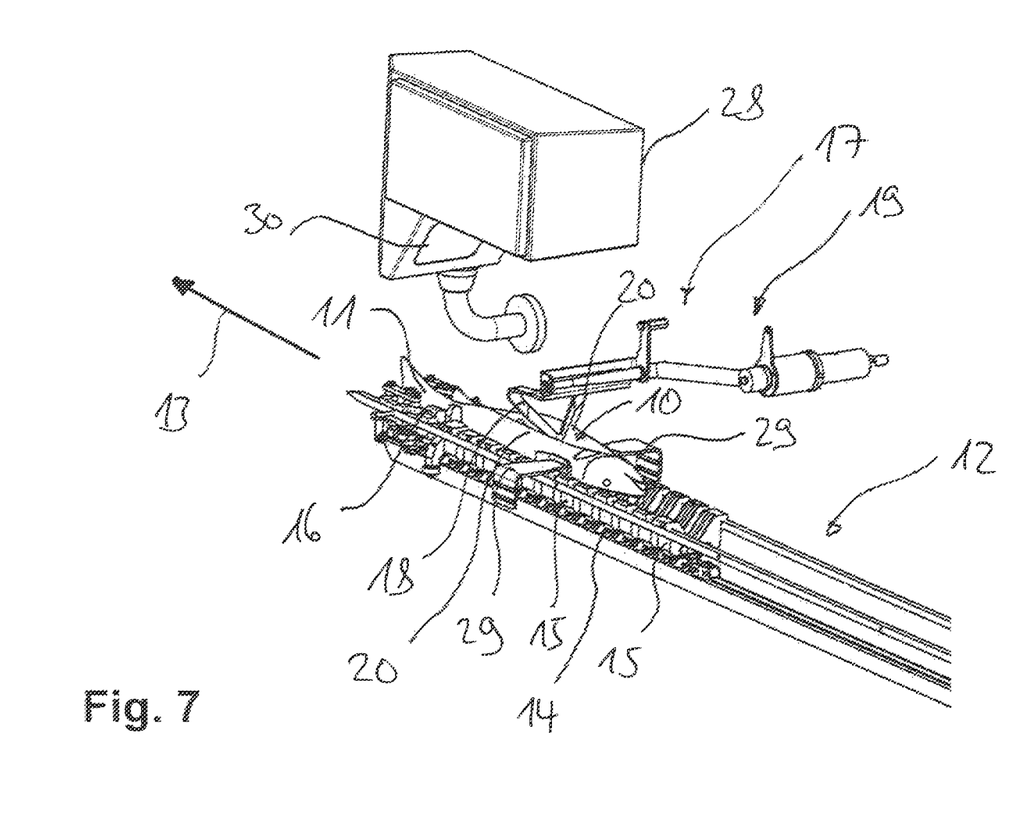

FIGS. 6 and 7 respectively show a perspective view of the detail views of FIGS. 4 and 5. FIGS. 4 to 7 each show a centring aid 29, by means of which the fish 11 are guided laterally and are thus centred in the middle.

The present invention further comprises an apparatus for gutting fish 11 which are conveyed along a processing line in the longitudinal direction 13 by means of the conveying device 12. The apparatus comprises opening tools configured for opening the abdominal cavity 10 of the fish 11, gutting tools designed for cleaning out the abdominal cavity 10 and an apparatus for subsequent optical inspection of the abdominal cavity 10 of the gutted fish 11 as described above. Such apparatuses for opening the abdominal cavity and the gutting tools are known, for example, from documents EP 1003378 A1 and EP 1411775 and are therefore not further described in detail.

The invention claimed is:

1. Method for optical inspection of gutted fish with opened abdominal cavity, comprising:
   conveying the fish along a processing line in the longitudinal direction utilizing a conveying device;
   pivoting of ventral flaps holding elements configured for holding open the abdominal cavity of the fish;
   taking of at least one sequence of images of abdominal cavity regions of one of the fish in each case, said image sequence comprising a plurality of single images taken using at least one optical imaging system arranged along the processing line;
   illuminating the abdominal cavity regions with light of in each case a predetermined spectral composition utilizing at least one illumination device, in each case at the times the single images are taken; and
   evaluating the image sequence according to prescribed quality parameters and removal of the relevant fish from the processing line by ejecting the relevant fish using an ejection device, should the evaluation reveal any deviation from the prescribed quality parameters.

2. Method according to claim 1, wherein the illumination takes place in each case with light of different spectral ranges at the times the images are taken.

3. Method according to claim 2, wherein the illumination takes place with light of a narrow band spectrum.

4. Method according to claim 2, further comprising overlaying the single images of the image sequence to create one overall image.

5. Method according to claim 1, wherein the time interval between taking two consecutive single images of one of the image sequences is chosen such that the two consecutive single images at least substantially illustrate the same abdominal cavity region.

6. Method according to claim 1, wherein each of the single images is taken with a separate optical imaging system.

7. Method according to claim 6, wherein each of the optical imaging systems is assigned a separate illumination device by way of which the illumination takes place in each case at the times the images are taken.

8. Method according to claim 1, wherein the single images are taken in black and white.

9. Method according to claim 6, wherein at least one of the single images is taken with one of the separate optical imaging systems with a viewing direction onto the abdominal cavity that is vertical or at least substantially vertical.

10. Method according to claim 9, wherein at least one other of the single images is taken with one other of the optical imaging systems with a viewing direction that is inclined in relation to the vertical viewing direction.

11. Method according to claim 10, wherein in the inclined viewing direction the images are taken towards the head of the fish.

12. Method for gutting fish which are conveyed along a processing line in the longitudinal direction utilizing a conveying device, opening of the abdominal cavity of the fish, cleaning out of the abdominal cavity utilizing gutting tools and subsequent optical inspection of the abdominal cavity of the gutted fish utilizing a method according to claim 1.

13. Apparatus for optical inspection of the opened abdominal cavity of gutted fish, comprising:
   a conveying device configured for conveying the fish along a processing line in the longitudinal direction;
   pivatable ventral flaps holding elements for holding open the abdominal cavity of the fish;
   at least one optical imaging system arranged along the processing line which is designed and configured to take at least one sequence of images of abdominal cavity regions of one of the fish in each case, said image sequence comprising a plurality of single images;
   at least one illumination device configured for illuminating the abdominal cavity regions, in each case with light of a predetermined spectral composition, in each case at the times the single images are taken; and
   an evaluation unit configured to evaluate the image sequence according to prescribed quality parameters, said evaluation unit being designed to activate an ejection device to remove the relevant fish from the processing line by ejecting the relevant fish, should the evaluation reveal any deviation from the prescribed quality parameters.

14. Apparatus according to claim 13, wherein the at least one illumination device is configured to illuminate the abdominal cavity region in each case with light of different spectral ranges, at the times the images are taken.

15. Apparatus according to claim 14, wherein the at least one illumination device comprises a light source which is configured to emit light of a narrow band spectrum.

16. Apparatus according to claim 13, further comprising a control designed and configured to control the at least one optical imaging system in such a way that the time interval between taking two consecutive single images of one of the image sequences is chosen such that the two consecutive single images at least substantially illustrate the same abdominal cavity region.

17. Apparatus according to claim 13, wherein a plurality of the optical imaging systems are each arranged and configured separately along the processing line to take each of the single images with one of said optical imaging systems.

18. Apparatus according to claim 17, wherein each of the optical imaging systems is assigned a separate illumination device which is configured to illuminate the abdominal cavity regions in each case at the times the images are taken.

19. Apparatus according to claim 13, wherein the at least one optical imaging system is designed as a black and white camera.

20. Apparatus according to claim 13, wherein the at least one optical imaging system is arranged in such a manner that at least one of the single images is taken with a viewing direction onto the abdominal cavity that is vertical or at least substantially vertical.

21. Apparatus according to claim 20, wherein at least one further optical imaging system is arranged in such a manner that at least one other of the single images is taken with a viewing direction that is inclined in relation to the vertical viewing direction.

22. Apparatus according to claim 21, wherein the at least one further optical imaging system is inclined in such a manner that in the inclined viewing direction the images are taken towards the head of the fish.

23. Apparatus according to claim 13, wherein the evaluation unit is configured to overlay the single images of the image sequence to create one overall image.

24. Apparatus for gutting fish which are conveyed along a processing line in the longitudinal direction utilizing a conveying device, comprising opening tools configured for opening the abdominal cavity of the fish, gutting tools designed for cleaning out the abdominal cavity and an apparatus for subsequent optical inspection of the abdominal cavity of the gutted fish according to claim 13.

* * * * *